United States Patent [19]

Vallejos et al.

[11] Patent Number: 5,223,621
[45] Date of Patent: Jun. 29, 1993

[54] TRANSVINYLATION OF CARBOXYLIC ACIDS

[75] Inventors: Jean-Claude Vallejos; Yani Christidis, both of Paris, France

[73] Assignee: Societe Francaise Hoechst, Puteaux, France

[21] Appl. No.: 817,194

[22] Filed: Jan. 6, 1992

[30] Foreign Application Priority Data

Jan. 4, 1991 [FR] France ............................ 91 00074

[51] Int. Cl.$^5$ .................................................. C11C 3/10
[52] U.S. Cl. ..................................... 554/165; 560/176; 560/217
[58] Field of Search ............... 554/165; 560/217, 176, 560/1

[56] References Cited

U.S. PATENT DOCUMENTS 3,755,387  8/1973  Young .................................. 554/165

OTHER PUBLICATIONS

McKean et al, Tetrahedron, vol. 28, pp. 233–238, 1972.
Ketterling et al, Applied Catalysis, vol. 66, pp. 123–132, 1990.

Primary Examiner—José G. Dees
Assistant Examiner—D. D. Carr
Attorney, Agent, or Firm—Browdy and Neimark

[57] ABSTRACT

Transvinylation process between vinyl acetate or vinyl propionate and a carboxylic acid of general formula (I), $$RCOOH \qquad (I)$$

in which R represents a substituted or non-substituted alkyl, cycloalkyl, aralkyl or aromatic radical, in the presence of a palladium catalyst, in which the catalyst is obtained in situ, by reacting, in the reaction medium, a derivative of palladium chosen from the group constituted by palladium II acetate, nitrate or hydroxide and palladium deposited on charcoal, with a tertiary amine chosen from the group constituted by 2,2′-bipyridyl, orthophenanthroline or tetramethylethylenediamine, that the quantity of palladium used, expressed in gram-atom of palladium II per 100 moles of carboxylic acid of general formula (I) is between 0.005 and 1 and that the quantity of amine is greater than 1 and less than 10 moles per gram-atom of palladium II used and use for the preparation of certain products.

3 Claims, No Drawings

TRANSVINYLATION OF CARBOXYLIC ACIDS

The present invention relates to a transvinylation process and its use.

Transvinylation reactions between vinyl acetate and a carboxylic acid are commonly carried out in the presence of one or more catalysts. As catalysts, the following have been successively suggested: mercuric salts, palladium catalysts, either in the presence or not of alkali metal salts and/or potassium hydroxide (German Patent No. 1127888, European Patent No. 54,154, Japanese Patent Applications Nos. 53(78)-127410 and 53(78)-77005), mixtures of palladium salts, copper and alkali metals (Japanese Patent Application No. 55(80)-104221 and German Patent Application No. 2823660) and finally, palladium catalysts complexed with specific tertiary bases such as diacetato-(2,2'-bipyridyl) palladium II, 1, or diacetato-(phenanthroline-1,10) palladium II, 2, described by T. A. Stephenson et al., J. Chem. Soc. 1965, 3632–40, and used as transvinylation catalysts by J. E. McKean et al, Tetrahedron, 1972, 28, 233–8.

These last catalysts, although active in transvinylation reactions are, however, unstable with heat: they are known to decompose at about 80° C. and, moreover, their preparation as described is difficult and/or expensive.

In order to avoid these disadvantages and to obtain an active catalyst, the palladium of which is easily recoverable at the end, the Applicant has discovered a transvinylation process between vinyl acetate or vinyl propionate and a carboxylic acid of general formula (I)

RCOOH (I)

in which R represents an alkyl, cycloalkyl, cycloalkylalkyl, aralkyl or aromatic radical, substituted or not, in the presence of a palladium catalyst, characterized by the fact that (1) this catalyst is obtained in situ by reacting a palladium derivative chosen from the group constituted by palladium II acetate, palladium II nitrate, palladium II hydroxide and palladium deposited on charcoal in the reaction medium with a tertiary amine chosen from the group constituted by 2,2'-bipyridyl, orthophenanthroline or tetramethylenediamine, (2) the quantity of palladium used, expressed in gram-atom of palladium II per 100 moles of carboxylic acid of general formula (I) is between 0.005 and 1 and (3) the quantity of amin is greater than 1 and less than 10 moles per gram-atom of palladium II used.

It may appear surprising that in the process according to the invention metallic palladium, deposited on charcoal, can be used, but it has been noted that said charcoal contains sufficient surface area of palladium II in the state of palladium II oxide to be able to be active.

In what has gone before, by alkyl radical is preferably meant a linear or branched alkyl radical containing 1 to 18 carbon atoms such as a methyl, ethyl, propyl, methylethyl, decyl radical etc . . . .

By cycloalkyl radical is preferably meant a radical containing 3 to 6 carbon atoms such as a cyclopropyl or cyclobutyl radical.

By cycloalkylalkyl radical is preferably meant a radical containing 4 to 7 carbon atoms such as a cyclopropylmethyl radical.

By aralkyl radical is preferably meant a radical containing 7 to 15 carbon atoms such as a benzyl or phenethyl radical.

By aromatic radical is preferably meant a radical containing 4 to 6 carbon atoms the nucleus of which contains 0, 1 or 2 heteroatoms, in this case preferably a sulphur or nitrogen atom, and there can be mentioned, for example, a phenyl or thienyl radical.

When the above radicals contain substituents, they are preferably linear or branched alkyl radicals containing 1 to 6 carbon atoms or alkoxy radicals containing 1 to 6 carbon atoms.

In the preferred conditions for implementation, the process described above is carried out:

at boiling point, in the presence of an excess of vinyl acetate or vinyl propionate, in the presence of 0.02 to 0.1 gram-atom of palladium II per 100 moles of carboxylic acid of general formula (I) employed, in the presence of 1.2 to 3 moles of 2,2'-bipyridyl, orthophenanthroline or tetramethylethylenediamine per gram-atom of palladium II employed, in the presence of a polymerization inhibitor such as phenothiazine; this can, for example, be used at the rate of 1 mmole per 100 moles of vinyl ester employed, by monitoring the progress of the reaction by the formation either of acetic acid or propionic acid according to whether vinyl acetate or propionate is used, in the presence of a catalyst obtained by reacting palladium II hydroxide with an excess of orthophenanthroline.

Palladium acetate or nitrate are commercially available products as is palladium deposited on charcoal; the palladium hydroxide is prepared according to the French Patent No. 1403398.

According to a variant of the process according to the invention, the palladium acetate, which is an expensive product, can be replaced advantageously by an equivalent quantity of a product of general formula II $(R_1—COO)_2Pd$ (II)

in which $R_1$ is a linear or branched $C_6$–$C_{12}$ alkyl radical, such that said $R_1$ radical corresponds for example with hexanoic, heptanoic, octanoic or lauric acid, and the palladium is in the PdII state.

The product of general formula (II) can be notably obtained from an alkali metal tetrachloropalladate by two methods, either by transforming the alkali metal tetrachloropalladate into palladium II hydroxide by the action of an alkali metal hydroxide then reacting it with an acid of general formula (III)

$R_1COOH$ (III)

where $R_1$ has the meaning given previously, or by reacting the alkali metal tetrachloropalladate with the same alkali metal salt of the acid of general formula (III), then by either method by extracting the corresponding product of general formula (III) from this aqueous medium with an organic solvent which is non-miscible with water. The preparation of palladium II hydroxide is described notably in the French Patent No. 1403398. In this way, palladium II hexanoate, palladium II heptanoate, palladium II octanoate and palladium II laurate were prepared by either method.

All these organometallic products are very soluble in non-polar aprotic solvents such as benzene, which facilitates their easy separation from their aqueous preparation medium.

The process according to the present invention is particularly advantageous for the preparation of vinyl esters of aliphatic or benzoic acids such as vinyl paratertiobutylbenzoate or vinyl laurate.

Moreover, the process according to the invention can be implemented up to a temperature of 100° C. At this temperature, the catalyst obtained according to the invention process remains stable and does not produce metallic palladium which is liable to be deposited in a more or less solid fashion on the walls of the reaction vessel. This stability with temperature is very important, because during the transvinylation reaction either acetic acid is formed when vinyl acetate is used, or propionic acid is formed when vinyl propionate is used, both of which have boiling points higher than 100° C. at ambient pressure. Moreover, at the end of the reaction, the paladium present in the reaction medium can be easily recovered, and recycled after treatment. This property is particularly useful for the industrial production of derivatives intended for the pharmaceutical or cosmetic industries using significant quantities of palladium, because the heavy metal content in these derivatives must be very low, taking into account the particular requirements of these industries.

The recovery of palladium present in the reaction medium can be carried out by precipitating it from the medium in the state of an insoluble complex which is then easily separated by filtration. This precipitation can be carried out notably, by additing to the reaction medium, either oxalic acid, or a tetraalkylammonium chloride in which the alkyl groups are $C_1$-$C_8$ optionally substituted by a phenyl group, or an anion exchange resin with quaternary ammonium chloride groups. After separation of the insoluble palladium complexes, a reaction medium containing less than 5 ppm of palladium is obtained. The desired vinyl ester is separated from this medium by known means, such as distillation. Advantageously, either 2 moles of tetraalkylammonium chloride, or 1 mole of oxalic acid, or finally a quantity of anion exchange resin whose exchange capacity is greater than 2 equivalents of chloride ions per gram-atom of palladium employed is used.

Finally a subject of the present Application is the use of the process described above for the preparation notably of vinyl paratertiobutylbenzoate, vinyl laurate and vinyl benzoate.

The following examples illustrate the invention without however limiting it.

In table 1, RCOOH has the meaning given previously, BP represents 2,2'-bipyridyl and OP represents orthophenanthroline. The quantities of carboxylic acid RCOOH and vinyl acetate are expressed in moles, the quantities of catalyst are expressed in $10^4$ moles. All the transvinylation reactions were carried out at boiling point, in the presence of 5 mmoles of phenothiazine per 100 moles of RCOOH acid. The yield is expressed relative to the theoretical value calculated from the RCOOH employed. The PdII content in the mother liquors, ML, is expressed in ppm.

EXAMPLES 1-4

1.774 g (10 mmoles) or palladium II chloride is dissolved in 3.58 g of 37% hydrochloric acid, being 36 mmoles, then this solution is diluted with 35 g of water. Then 13 g of water containing in solution 2.8 g (70 mmoles) of sodium hydroxide is introduced into this solution, under agitation while maintaining the temperature below 35° C., then 8.8 g of octanoic acid (50 mmoles) is introduced over 15 minutes at a temperature lower than 35° C. The reaction medium is then left for 15 minutes at ambient temperature then extracted twice with 10 g of toluene.

The organic extraction phases are then washed with water, then they are reunited and dried over anhydrous sodium sulphate. In this way 26.5 g of a toluene solution containing 4.2±0.1% of palladium II is obtained for a theoretical titer of 4.1% in the palladium II octanoate state: $Pd(OCOC_7H_{15})_2$. This catalyst is designated $C_{8-1}$.

Similarly, starting from hexanoic acid, palladium II hexanoate designated $C_{6-1}$, is prepared and starting with heptanoic acid, palladium II heptanoate designated $C_{7-1}$, is prepared.

EXAMPLE 5

1.774 g (10 mmoles) of palladium II chloride is dissolved in 3.58 g of 37% hydrochloric acid, being 36 mmoles, then the solution is diluted with 35 g of water. 7.2 g of an aqueous solution containing 1.44 g (36 mmoles) of sodium hydroxide is introduced over 15 minutes into this cooled solution and the temperature is maintained at less than 30° C. In this way an aqueous solution of sodium tetrachloropalladate is obtained. Then 4 g (20 mmoles) of lauric acid dissolved in 46 g of toluene is introduced into this solution, then 4 g of an aqueous solution containing 0.8 g (20 mmoles) of sodium hydroxide is introduced over 10 minutes at 30° C. under agitation. After agitating for 3 hours the reaction medium is decanted then the aqueous phase is washed twice with 15 g of toluene and then the organic phases are reunited. In this way about 79 g of a toluene solution containing palladium II laurate is obtained having a titer of 1.28% palladium II (theoretical 1.34%). This catalyst is subsequently designated $C_{12-2}$.

Similarly, toluene solutions containing palladium II hexanoate are prepared.

EXAMPLE 6

A solution constituted by :
178 g (1 mole) of paratertiobutylbenzoic acid,
430 g (5 moles) of vinyl acetate,
0.21 g (0.93 mmole) of palladium acetate,
0.43 g (2.75 mmoles) of 2,2'-bipyridyl,
0.01 g (0.05 mmole) of phenothiazine,
is heated for 12 hours under reflux, then the reaction solution is cooled down to 20° C. 0.12 g (0.95 mmole) of oxalic acid crystallized with two water molecules is introduced under agitation at this temperature, then the reaction medium is left for two hours under agitation at 20° C. The precipitate formed is separated by filtration and the filtrate is distilled under reduced pressure. In this way 151.2 g (0.75 mole) of vinyl paratertiobutylbenzoate is obtained, distilling at 110±3 °C. under a vacuum of 6.6 mbar, which represents a yield of 75% of the theoretical value.

EXAMPLES 7-21

By operating according to Example 6 starting with the raw materials and under the operating conditions mentioned in table 1, the vinyl esters of the acids mentioned in table 1 are obtained with the yields indicated.

TABLE 1

| | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|
| Vinyl acetate | 5 | 5 | 5 | 350 | 2.5 | 2.5 | 1.25 | 2.5 | 5 | 5 | 5 | 5 | 1.25 | 5 | 2.5 | 1.25 |
| RCOOH | | | | | | | | | | | | | | | | |
| nature | TA | LA | BA | TA | TA | LA | TA | BA | BA | BA | BA | BA | BA | BA | TA | TA |
| quantity | 1 | 1 | 1 | 70 | 0.5 | 0.5 | 0.25 | 0.5 | 1 | 1 | 1 | 1 | 0.25 | 1 | 0.5 | 0.25 |
| Catalyst | | | | | | | | | | | | | | | | |
| Pd II acetate | 9 | 2.34 | 10 | 163.9 | | | | | | | | | | | | |
| Pd II hydroxide | | | | | 1.15 | 1.15 | 1.15 | 1.15 | | | | | | | | |
| Other catalyst | | | | | | | | | | | | | | | | |
| nature | | | | | | | | | $C_{8-1}$ | $C_{6-1}$ | $C_{7-1}$ | $C_{12-2}$ | B | A | C | D |
| quantity | | | | | | | | | 10 | 10 | 10 | 10 | 2.5 | 10 | 16.5 | 58.7 |
| BP | 27.5 | | | | | | 1.75 | | | | | | | | | |
| OP | | 3.5 | 15 | 246 | 1.75 | 1.75 | | 1.75 | 15 | 15 | 15 | 15 | 3.75 | 15 | 17.5 | 176.1 |
| duration (hour) | 12 | 20 | 6 | 24 | 20 | 20 | 15 | 20 | 6 | 6 | 6 | 6 | 6 | 6 | 20 | 24 |
| yield (%) | 75 | 83 | 89 | 81 | 79 | 79.4 | 79.6 | 83.7 | 83.7 | 83.6 | 85.3 | 84.4 | 83,5 | 2 | 21 | 83.7 |

Notes on Table 1

TA : paratertiobutylbenzoic acid
LA : lauric acid
BA : benzoic acid
A : palladium II chloride used in the presence of 10 moles of sodium acetate per mole of palladium II chloride
B : palladium II nitrate
C : palladium II oxide; $PdO, H_2O$
D : palladium II hydroxide prepared according to FR 1403398 titrating at 11.4% by weight of palladium II
$C_{6-1}$ : palladium II hexanoate prepared in Example 2
$C_{7-1}$ : palladium II heptanoate prepared in Example 3
$C_{12-2}$ : palladium II laurate prepared in Example 5
D : palladium deposited on charcoal at 5% by weight sold by the JOHNSON MATHEY company under the reference 38H.

The amounts of vinyl acetate and RCOOH are expressed in moles, whereas the amounts of the products used to prepare the catalyst are expressed in 0.1 mmole.

EXAMPLE 22

A mixture containing:
12.46 kg (70 moles) of paratertiobutylbenzoic acid
30.1 kg (350 moles) of vinyl acetate
3.68 g (16.4 mmoles) of palladium II acetate
4.43 g (24.6 mmoles) of orthophenanthroline
0.7 g (3.5 mmoles) of phenothiazine,
is heated under reflux for 24 hours, then the reaction solution is cooled down to 20° C. 7.62 g (33.45 mmoles) of triethylbenzylammonium chloride is introduced under agitation at this temperature and the reaction medium is left for 2 hours under agitation at 20° C. The precipitate formed is then separated by filtration. In this way 6.2 g of orthophenanthroline - palladium chloride complex is separated out and 4 ppm of palladium II is analyzed in the filtrate. After treating the filtrate, 11.5 kg (56.7 moles) of vinyl paratertiobutylbenzoate is obtained, distilling at 110±3° C. under 6.6 mbar, representing a yield of 81% of the calculated theoretical value relative to the paratertiobutylbenzoic acid.

EXAMPLE 23

Example 22 is repeated, but at the end of the reaction the triethylbenzylammonium chloride used is replaced by 0.89 g (7.06 mmoles) of oxalic acid crystallized with two water molecules. In this way a filtrate containing 3 ppm of palladium is obtained after filtration of the comples formed.

EXAMPLE 24

Example 22 is repeated, but at the end of the reaction the triethylbenzylammonium chloride used is replaced by 140 g of moist A26 resin which is commercially available from the ROHM and HAAS Company and is based on quaternary ammonium chloride. In this way a filtrate containing 2 ppm of palladium II is obtained after filtration of the resin.

We claim:

1. Transvinylation process between vinyl acetate or vinyl propionate and a carboxylic acid of formula (I),

RCOOH  (I)

in which R represents a substituted or non-substituted alkyl, cycloalkyl, aralkyl or aromatic radical, in the presence of a palladium catalyst, wherein (1) said catalyst is obtained in situ, by reacting, in the reaction medium, a derivative of palladium selected from the group consisting of palladium II acetate, palladium II nitrate, palladium II hydroxide and palladium deposited on charcoal, with a tertiary amine selected from the group consisting of 2,2'-bipyridyl, orthophenanthroline, and tetramethylethylene-diamine, (2) the quantity of palladium used, expressed in gram-atom of palladium II per 100 moles of said carboxylic acid of formula (I) is between 0.005 and 1, and (3) the quantity of amine is greater than 1 and less than 10 moles per gram-atom of palladium II used; and recovering palladium in the form of a complex by reaction with oxalic acid.

2. Transvinylation process between vinyl acetate or vinyl propionate and a carboxylic acid of formula (I),

RCOOH  (I)

in which R represents a substituted or non-substituted alkyl, cycloalkyl, aralkyl or aromatic radical, in the presence of a palladium catalyst, wherein (1) said catalyst is obtained in situ, by reacting, in the reaction medium, a derivative of palladium selected from the group consisting of palladium II acetate, palladium II nitrate, palladium II hydroxide and palladium deposited on charcoal, with a tertiary amine selected from the group consisting of 2,2'-bipyridyl, orthophenanthroline, and tetramethylethylene-diamine, (2) the quantity of palladium used, expressed in gram-atom of palladium II per 100 moles of said carboxylic acid of formula (I) is between 0.005 and 1, and (3) the quantity of amine is greater than 1 and less than 10 moles per gram-atom of palladium II used; and recovering palladium in the form of a complex by reaction with a tetraalkylammonium chloride in which the alkyl groups contain $C_1$-$C_8$ optionally substituted by a phenyl group.

3. Transvinylation process between vinyl acetate or vinyl propionate and a carboxylic acid of formula (I), $$RCOOH \qquad (I)$$

in which R represents a substituted or non-substituted alkyl, cycloalkyl, aralkyl or aromatic radical, in the presence of a palladium catalyst, wherein (1) said catalyst is obtained in situ, by reacting, in the reaction medium, a derivative of palladium selected from the group consisting of palladium II acetate, palladium II nitrate, palladium II hydroxide and palladium deposited on charcoal, with a tertiary amine selected from the group consisting of 2,2'-bipyridyl, orthophenanthroline, and tetramethylethylene-diamine, (2) the quantity of palladium used, expressed in gram-atom of palladium II per 100 moles of said carboxylic acid of formula (I) is between 0.005 and 1, and (3) the quantity of amine is greater than 1 and less than 10 moles per gram-atom of palladium II used; and recovering said palladium in the form of a complex by reacting it with an ion exchange resin having quaternary ammonium chloride groups.

* * * * *